United States Patent [19]

Wilson et al.

[11] Patent Number: 5,595,711
[45] Date of Patent: Jan. 21, 1997

[54] ISOLATED BIOLOGICAL AND MEDICAL WASTE PROCESSOR AND LID LINER CARRYING A CHEMICALLY SENSITIVE DECONTAMINANT

[75] Inventors: Joseph H. Wilson, Speedway; David C. Haeberle, Bloomington, both of Ind.; Raymond C. Kralovic, Willoughby, Ohio; Kenneth R. Lamaster, Indianapolis, Ind.; David B. Mennel; Jeffrey C. Rapp, both of Greenwood, Ind.; Lewis I. Schwartz, Bratenahl; Kathleen M. Antloga, Chardon, both of Ohio

[73] Assignees: Ecomed, Inc., Indianapolis, Ind.; Steris Corporation, Mentor, Ohio

[21] Appl. No.: 504,920

[22] Filed: Jul. 20, 1995

Related U.S. Application Data

[63] Continuation-in-part of Ser. No. 209,944, Mar. 11, 1994, abandoned.

[51] Int. Cl.[6] .................................................. G01N 31/22
[52] U.S. Cl. .................. 422/119; 220/400; 220/369; 241/606; 588/258; 588/260; 588/900; 436/1; 422/184.1
[58] Field of Search ........................... 436/1; 422/56–61, 422/119, 184; 220/400, 403, 404, 470, 369, 371, 908; 241/606; 588/260, 258, 900; 116/206

[56] References Cited

U.S. PATENT DOCUMENTS

| | | | |
|---|---|---|---|
| 2,635,784 | 4/1953 | Bering et al. | 220/44 |
| 2,656,985 | 10/1953 | Backlund et al. | 241/88 |
| 2,820,595 | 1/1958 | Schumacher | 241/99 |
| 2,912,176 | 11/1959 | Jordan | 241/194 |
| 3,181,802 | 5/1965 | Lung et al. | 241/257 |
| 3,186,652 | 6/1965 | Hardy et al. | 241/257 |
| 3,211,389 | 10/1965 | Sherman, Jr. | 241/257 |
| 3,386,668 | 6/1968 | Shepherd | 241/606 |
| 3,436,029 | 4/1969 | Lopp et al. | 241/194 |
| 3,528,469 | 9/1970 | Mantelet | 146/68 |
| 3,901,349 | 8/1975 | DeNoyer | 181/33 |
| 4,269,364 | 5/1981 | Moriconi et al. | 241/36 |
| 4,275,848 | 6/1981 | Webb, Sr. | 241/66 |
| 4,526,752 | 7/1985 | Perlman et al. | 422/56 |
| 4,586,666 | 5/1986 | Fox | 241/282.2 |
| 4,637,561 | 1/1987 | Edberg | 241/154 |
| 4,746,616 | 5/1988 | Honigs | 436/1 |
| 4,765,499 | 8/1988 | von Reis et al. | 215/261 |
| 4,816,307 | 3/1989 | Honeycutt | 428/34.1 |
| 4,860,916 | 8/1989 | Winters | 220/403 |
| 4,955,548 | 9/1990 | Rahill | 241/30 |
| 4,971,261 | 11/1990 | Solomons | 241/99 |
| 4,973,005 | 11/1990 | Haesebrouck et al. | 241/194 |
| 4,984,748 | 1/1991 | Kimura | 241/65 |
| 5,018,675 | 5/1991 | Gateaud | 241/282.2 |
| 5,054,696 | 10/1991 | Mennel et al. | 241/34 |
| 5,089,228 | 2/1992 | Meijer | 422/37 |
| 5,236,135 | 8/1993 | Wilson et al. | 241/21 |
| 5,240,187 | 8/1993 | Wilson | 241/21 |

FOREIGN PATENT DOCUMENTS

| | | |
|---|---|---|
| 1394972 | 3/1965 | France . |
| 61-025432A | 2/1986 | Japan . |
| 725700 | 4/1980 | U.S.S.R. . |
| 1142167A | 2/1985 | U.S.S.R. . |
| 1546076A1 | 2/1990 | U.S.S.R. . |
| WO92/20450 | 11/1992 | WIPO . |
| WO94/29028 | 12/1994 | WIPO . |
| WO95/24227 | 9/1995 | WIPO . |

*Primary Examiner*—Jill Warden
*Assistant Examiner*—Jan M. Ludlow
*Attorney, Agent, or Firm*—Brinks Hofer Gilson & Lione

[57] ABSTRACT

A processing chamber for the treatment and decontamination of biological or medical waste includes a rotating waste treatment system carried within an open-top processing chamber, a cap for closing the chamber opening, a gas-pervious liner carried within the chamber for preventing waste from adhering to the underside of the cap as a result of waste-treatment operations, a sealing member disposed at and for sealing the interface of the cap and the processing chamber, and a chemical indicator carried within the interior of the processing chamber for confirming the presence of decontaminant during a waste treatment cycle.

43 Claims, 6 Drawing Sheets

ISOLATED BIOLOGICAL AND MEDICAL WASTE PROCESSOR AND LID LINER CARRYING A CHEMICALLY SENSITIVE DECONTAMINANT

RELATED APPLICATIONS

This application is a continuation-in-part of U.S. Ser. No. 08/209,944, filed Mar. 11, 1994, now abandoned.

FIELD OF THE INVENTION

This invention relates generally to an apparatus for handling and treating biological waste materials, and more particularly, to such an apparatus including a cap liner and an indicating means for confirming the decontamination of the medical waste without exposing medical personnel to potentially infectious waste.

BACKGROUND OF INVENTION

U.S. Pat. Nos. 5,236,135 and 5,240,187 disclose methods and apparatus for the treatment of solid and non-solid (soft) biological waste materials that permits the collection of such biological waste at the point and at the time of its generation in a container, which is subsequently transported for pulverization, decontamination and safe disposal. A separate portable processing chamber, with an integral means to treat biological waste, is used at locations remote from a main power unit for the collection of biological waste and is then moved to the location of the main power unit to drive the waste-treatment means carried within the chamber. The separate portable processing chamber includes a closable chamber, a rotatable waste treatment system carried within the chamber and a plurality of pivotable blades carried by the rotatable system which interact with the biological waste and surfaces formed on the chamber walls and provide effective disintegration and blunting of solid waste, cutting and mincing of non-solid waste, and decontamination of the biological waste within the processing chamber.

While biological waste can be effectively treated by the method and apparatus of U.S. Pat. Nos. 5,236,165 and 5,240,187, treated biological waste particles can sometimes adhere and cling to the under surfaces of the cap or lid that closes the processing chamber, and such waste particles can drop uncontrollably from the cap or lid as, or after, it is removed from the apparatus. Although such biological waste will generally be decontaminated as a result of its treatment within the processing chamber, its escape onto adjacent surfaces requires clean-up and is undesirable. In addition, if the processing chamber is mistakenly opened before treatment and decontamination of the biological waste is completed, the escape of such biological waste can require special precautions to avoid exposure of personnel to undecontaminated and possibly infectious biological waste.

To further safeguard the personnel handling the processing and disposal of such biological waste, it is desirable to have an indication that the decontamination agent was present in the treatment process, or when decontamination of the biological waste has been effected.

SUMMARY OF THE INVENTION

The invention comprises a waste treatment apparatus including a processing chamber for the treatment and decontamination of biological waste, including such solid items as syringes and needles, glassware, tubes, vials, culture plates and specimens, and disposable scalpels, and such soft and fibrous materials as gloves, masks and bandage and gauze materials, which has been provided with means for preventing biological waste from adhering to the underside surface of the cap or lid of the processing chamber as a result of its operation, and, preferably, provided with means for indicating the presence of decontaminant in the waste treatment cycle. Preferably, such an indicator means is provided by the means for preventing biological waste from adhering to the underside of the cap or lid in the waste treatment cycle.

The apparatus of the invention comprises a separate waste treatment assembly including a chamber for the collection, disintegration and decontamination of soft and hard biological waste. The apparatus comprises a chamber forming means forming an upper opening, with a waste treatment system rotatably carried within the interior of the chamber. The apparatus further comprises a cap or lid for engaging and closing the upper opening of the chamber to define a closed waste treatment chamber, and a liner carried atop the upper opening within the processing chamber for preventing the biological and/or medical waste from adhering to the underside of the cap or lid and providing a signal that the biological waste has been exposed to decontaminant as a result of its treatment within the waste treatment chamber.

More specifically, a preferred apparatus includes a chamber having a bottom and a cylindrical sidewall forming, by an opening interface, an upper opening. The cap of the waste treatment assembly comprises a lid with a central panel having a circumferential lip for receiving a sealing member such as an O-ring. The opening interface of the chamber sidewall forming the upper opening of the chamber more specifically comprises a peripheral flange disposed at the upper edge of the sidewall of the processing chamber circumferentially about the upper opening. The flange is selectively dimensioned so as to be received within the circumferential lip of the cap to engage the O-ring therein.

The liner and, preferably, an indicator means, are adapted to be carried by the apparatus by pressure surfaces of the lid and chamber sidewall when the lid sets atop the sidewall of the chamber to separate the underside of the lid from the processing chamber interior. The apparatus further includes means, such as a plurality of latches, for securing the lid over the upper opening of the chamber and for effecting the sealing engagement of the lid, chamber sidewall and O-ring. The liner is disposable without human contact upon completion of the treatment cycle and provides a signal that the biological waste has been exposed to decontaminant. In a preferred apparatus of the invention, the waste treatment chamber includes a HEPA filter carried by the lid and the liner is gas pervious to permit the escape of air and water vapor from the interior of the chamber during operation of the apparatus.

The decontaminant indicator is preferably a chemically sensitive indicator carried within the interior of the chamber that reacts to a decontaminant present within the chamber during the waste treatment cycle, and generates an output indicating that decontaminant was present. The indicator can be carried by or impregnated into a gas-permeable membrane liner adjacent the underside of the cap.

In a further preferred embodiment, the cap liner comprises a semi-rigid thin fiberboard disk having at least two orifices formed therein wherein the chemical indicator is carried atop the disk so as to cover one of the orifices while the second orifice permits aerosols and fine particulates from within the chamber interior to pass therethrough. The indicator can be defined by a patch of fibrous material carrying impregnated chemically sensitive solution. A transparent barrier is disposed over the chemical indicator to reduce its absorption rate while still allowing for the observation of the output signal generated by the indicator.

In an even further preferred embodiment, the cap liner comprises a semi-rigid thin fiberboard disk having at least one orifice formed therein for allowing aerosols and fine particulates from within the chamber interior to pass therethrough, a liquid-impervious coating or plasticizer applied to at least one side thereof, and a relatively small area of the coated side of the disk having no liquid-impervious coating applied thereto. The small coating-free area on the coated side of the disk allows liquids to absorb into the cap liner generally at that area during the waste treatment cycle. Applied to that general area on the reverse uncoated side of the disk is a chemically sensitive indicator solution so that as the liquid and decontaminant from the interior of the treatment chamber splashes up onto the underside of the liner, it is slowly absorbed into the fiberboard material at the small coating-free area, whereupon the chemically sensitive indicator solution, which was previously impregnated within the fiberboard material, will chemically react with decontaminant present in the waste liquid and present an observable output signal confirming the presence of decontaminant during the treatment cycle.

Other features and advantages of the disclosed embodiments and methods of the invention will be apparent from the drawings and more detailed description of the invention that follows.

Figure 2:
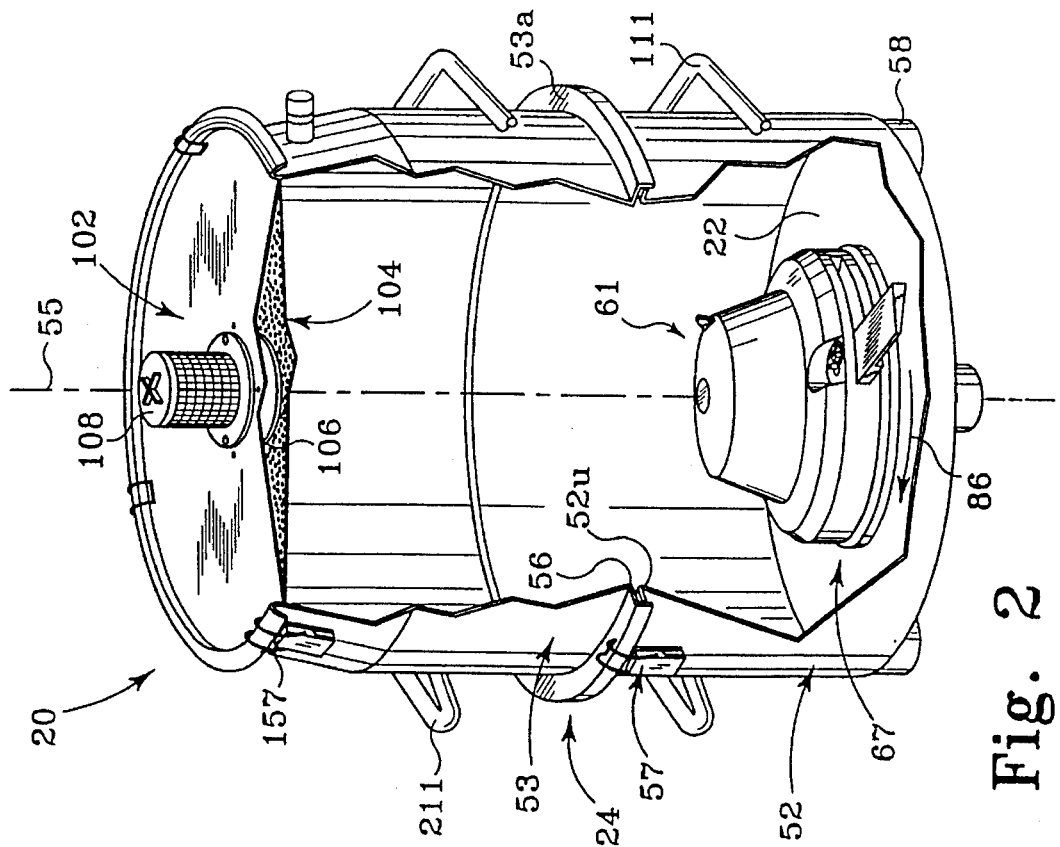
FIG. 2 is a partially cut-away perspective view to show a use of the invention in the apparatus of FIG. 1.

DESCRIPTION OF THE PREFERRED EMBODIMENT AND BEST MODE FOR CARRYING OUT THE INVENTION

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 1:
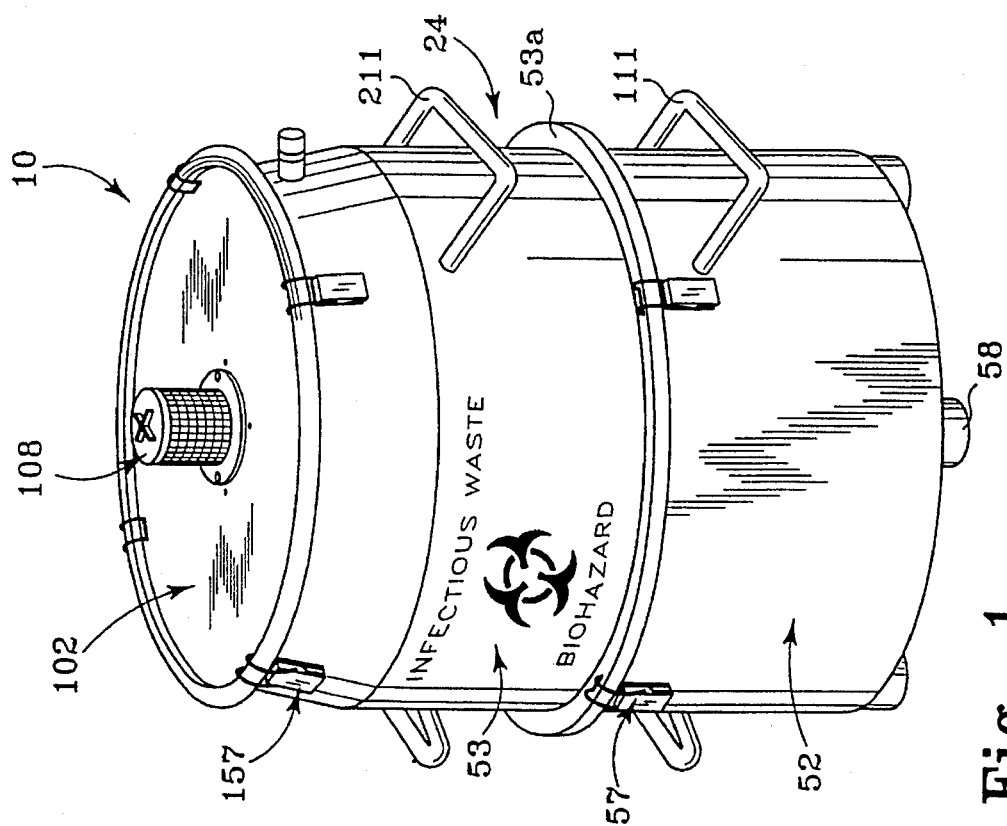
FIG. 1 is a perspective view of a fully assembled waste collection and processing apparatus that may include the invention.

Referring now to the drawings, and particularly to FIGS. 1 and 2, a waste treatment apparatus 10 includes a chamber 20, preferably including a bottom wall 22 and an upwardly standing, generally cylindrical sidewall 24 having a circumferential upper edge 54 forming an open top 26. Chamber 20 can be made integral or can include a lower kettle-like housing 52 and a top cylindrical housing 53, both of which are symmetrical about a central axis 55.

Where, as shown, chamber 20 includes a lower kettle-like housing 52 and a top housing 53, lower housing 52 can have an outwardly turned upper circular flange 52U (FIGS. 2 and 3) supporting a first sealing member such as an O-ring 56, which engages the circular bead 53a at the bottom of the top housing 53. The top and lower housings 52, 53 can be fastened together by base latches 57 defined by over-center, lever operated, spring clamps such as are available from Dzus Fasteners of West Islip, N.Y. 11795. The bottom of lower housing 52 preferably can have four circularly spaced feet 58 for supporting the chamber assembly on a counter, and for preventing the chamber 20 from rotating while operatively disposed in the main power cabinet. Pairs of U-shaped handles 111 and 211 may also be provided on the sides of the lower housing 52 and upper housing 53, respectively, for purposes of handling and transporting the apparatus 10.

As shown in FIG. 2, a rotatable waste treatment assembly 61 is carried within chamber forming means 20. Such a waste treatment assembly may comprise an impeller assembly 61 mounted adjacent the bottom floor 22 of the lower housing 52. The rotatable waste treatment assembly 61 can be supported by a bearing mount cylinder (not shown) which can be welded to the bottom 22 of lower housing 52 around a central opening (not shown) provided in the bottom 22. Inasmuch as the manner in which the waste treatment assembly 61 is constructed, driven or is carried within the chamber, forms no part of the present invention, such details are not given here; however, U.S. Pat. Nos. 5,236,135 and 5,240,187 describe such waste treatment apparatus.

In the treatment and decontamination of biological waste with such apparatus, the cap or lid 102 is removed from the chamber forming means 20 and biological waste to be treated is placed in the chamber forming means 20, preferably accompanied by a decontaminant solution. The cap or lid 102 is then replaced and secured to the chamber-forming means 20 by one or more of the fasteners 157. The apparatus 10 is then connected with a power unit, which, in operation, rotates the waste treatment assembly 61. Rotation of the waste treatment assembly disintegrates the biological waste by pulverizing and blunting solid waste and cutting and tearing soft waste and washes the waste particles with decontaminant solution.

In operation, however, the waste particles are thrown about in the interior of chamber forming means 20 and many such particles are thrown against and may adhere or cling to the underside of lid 102. When the lid 102 is subsequently removed from the chamber forming means 20, generally at the conclusion of the waste treatment cycle, waste particles that may adhere to the underside of lid 102 may be dislodged as, or after, lid 102 is removed and fall uncontrolled on surfaces adjacent the apparatus 10. Such waste particles present a cleaning problem, and, if, for some reason, treatment is stopped and lid 102 is removed from the apparatus before decontamination has been completed, such escaping waste particles may also present a decontamination problem due to the exposure of personnel to possibly undecontaminated biological or medical waste.

The invention provides such a waste treatment apparatus, as shown in FIGS. 2–5, further including means for preventing waste particles from adhering to the underside of the lid as a result of operation of the apparatus, and, preferably, means for indicating to personnel whether decontaminant was present in the waste treatment cycle when the lid is removed from the apparatus but before operating personnel are exposed to possibly infectious waste materials within the waste treatment chamber.

Figure 3:
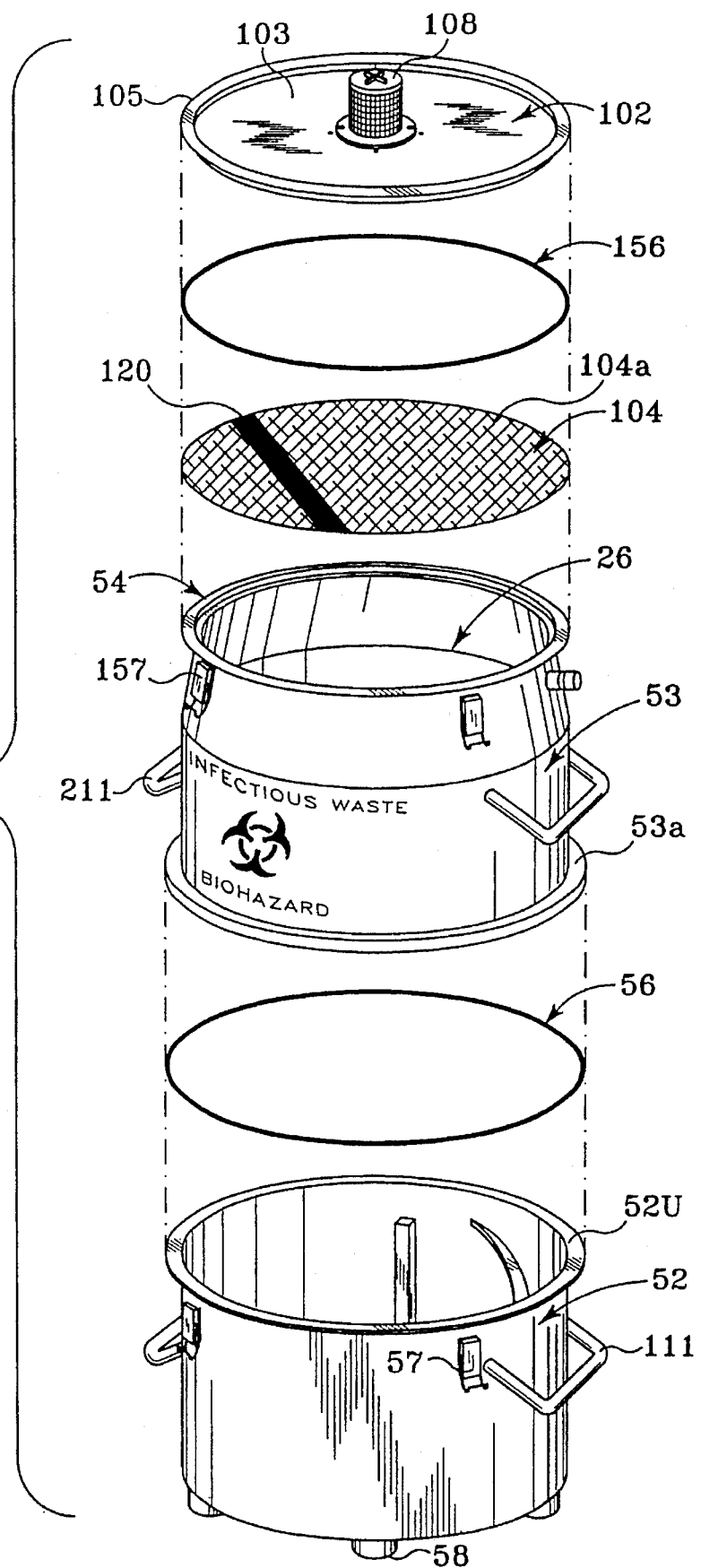
FIG. 3 is an exploded perspective view of the apparatus of FIG. 2 to show the invention more clearly.
Figure 4:
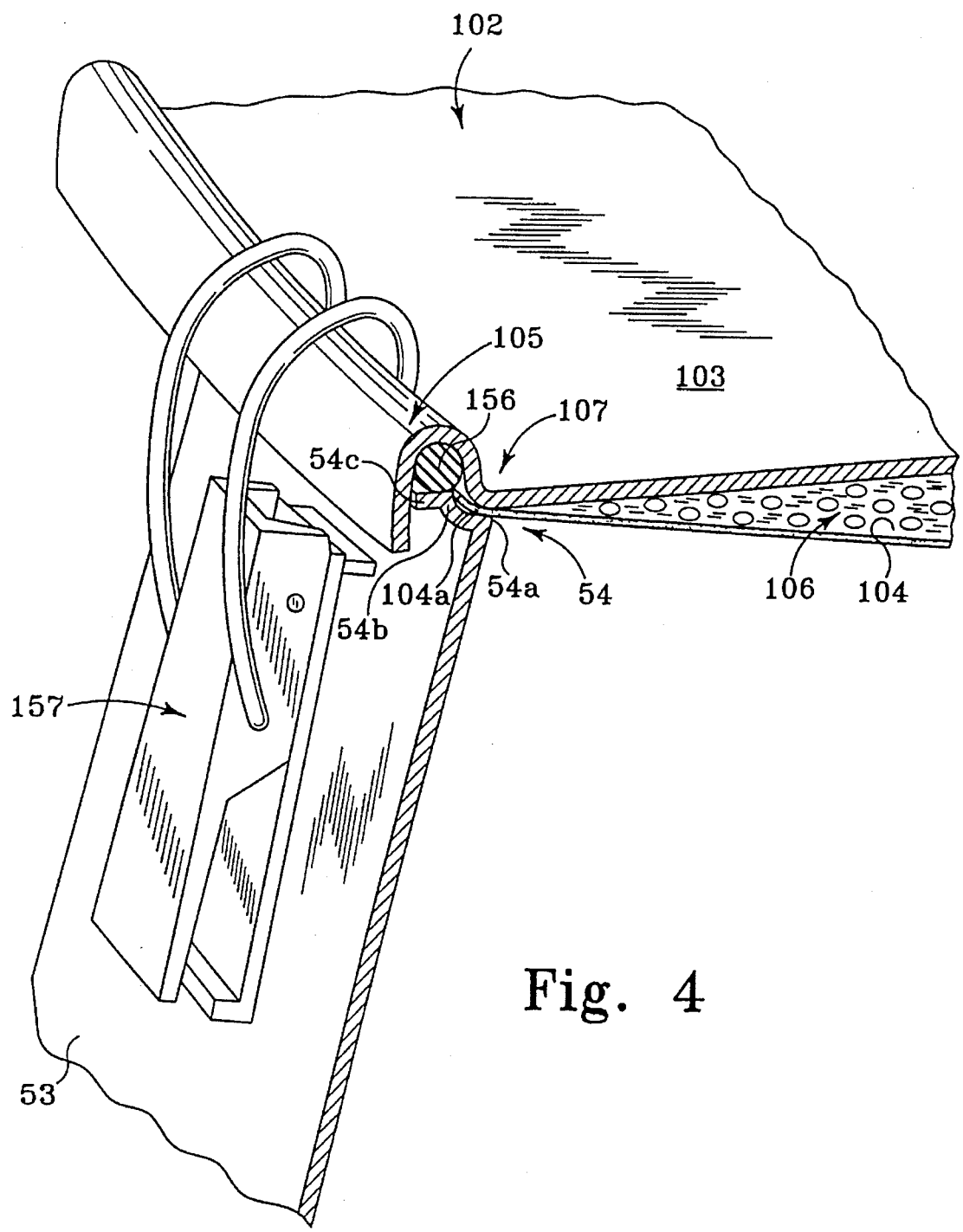
FIG. 4 is an enlarged, isolated partial cross-sectional view of the interface between the cap, the liner, the O-ring and the upper edge of the sidewalls of a portable processing chamber to more clearly show one preferred embodiment of the invention.

Referring particularly to FIGS. 3 and 4, the top housing 53 of processing chamber 20 includes a cap or lid 102 having a central panel 103 and a generally circumferential edge or lip 105. Lip 105 comprises a downwardly facing U-shaped cross section, as shown in FIG. 4 to receive an O-ring 156. Lid 102 is positioned atop and fastened via clamps 157 to the top housing 53 thereby closing upper opening 26 of chamber 20.

The opening 26 of the upper housing 53 is more specifically formed by an opening interface in the form of a circumferential flange 54 (FIGS. 3 and 4) selectively dimensioned so as to be received within the downwardly facing U-shaped lip 105 of cap 102. Referring particularly to FIG. 4, lid 102 further includes a downwardly-facing pressure surface 107 defined by the transition interconnecting the central panel 103 to the circumferential lip 105 of cap 102. The opening interface 54 of the upper housing 53 includes an upwardly facing pressure surface 54b. The upwardly facing pressure surface 54b is formed outwardly from the sidewall of top housing 53 and provides a transition interconnected with a generally planar circumferential annular flange portion 54c. Pressure surface 107 of cap 102 coacts with the pressure surface 54b to engage therebetween the circumferential edge 104a of liner 104, thereby providing means for securing the liner 104 in position to separate the underside of cap 102 from the processing chamber. O-ring 156 is engaged in a sealing relationship within the peripheral lip 105 of cap 102 by the circumferential annular flange portion 54c of the opening interface 54 to prevent the escape of material at that interface.

Figure 5:
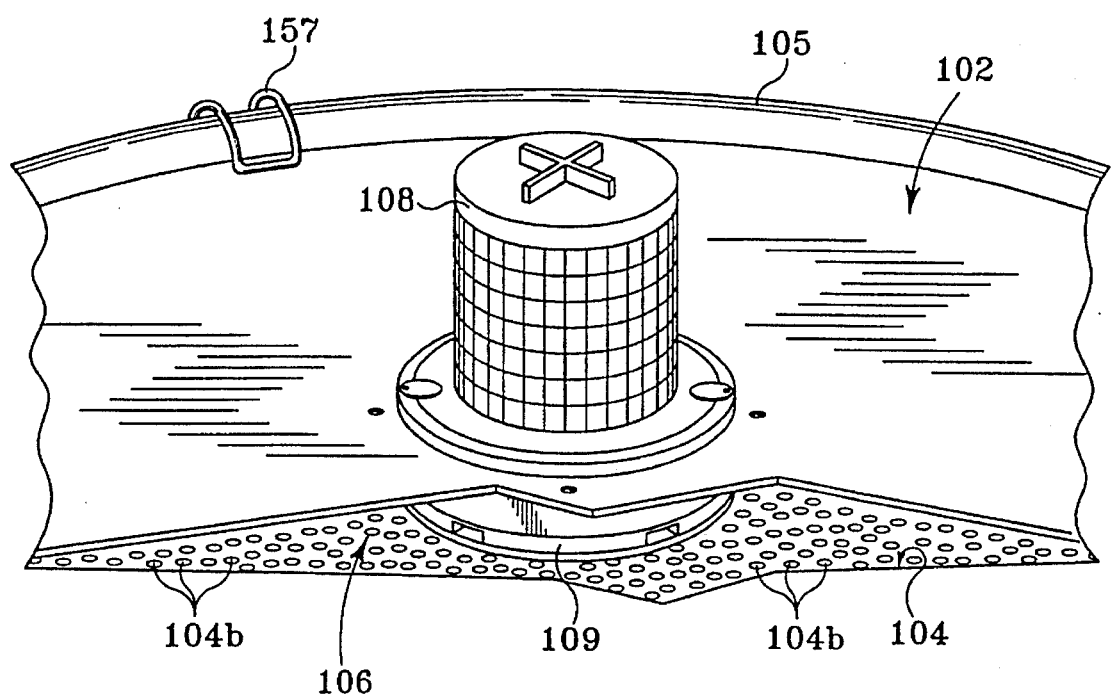
FIG. 5 is an enlarged, isolated partial cross-sectional view of the cap, filter and liner of the apparatus as shown in FIG. 2.

Means for preventing adherence of waste material particles to the underside of lid 102 is thus provided by a cap liner 104 disposed adjacent the underside of cap 102 to prevent waste material particles from being thrown against and adhering to the underside of the cap. In one preferred embodiment as best shown in FIG. 5, a plenum-like space 106 is formed between cap 102 and liner 104. Cap liner 104 is preferably formed by a gas-permeable material that permits the closed processing chamber 20 to breath through the entire cap liner 104, by virtue of a plurality of small or fine openings or orifices 104b provided in liner 104, and ultimately through a HEPA filter 108 during the operation of the apparatus. The plurality of small orifices 104b permit aerosols and fine particulate matter generated during the treatment cycle to pass through the membrane liner 104 while preventing waste liquids and solids from passing therethrough. A suitable gas-permeable material is the relatively flexible No. 8060 Spunbonded Polyester, available from Filter Fabrics Inc., which provides openings in the interstices between the bonded fibers.

Preferably, an indicator means 120 (FIG. 3) is carried within the interior of chamber 20 by the liner 104. Indicator means 120 is preferably a chemically sensitive indicator that reacts to decontaminant in the processing chamber during operation to generate a color-change output signal indicating that the decontaminant was present in the chamber. The indicator 120 can be carried by the top of the liner 104 to be readily observable to a person when the lid 102 is removed and before processing chamber 20 is completely opened by removal of liner 104. Alternatively, the indicator 102 can be impregnated into the liner 104. The selection of an indicator material depends, generally, upon the decontaminant material that is used to treat the biological or medical waste. When used with a decontaminating agent including peracetic acid, one such suitable chemically sensitive indicator is Peracetic Acid Indicator, manufactured by Serim Research located in Elkhart, Ind., and having a product name "Chronegenic Oxidation Sensitive Indicator."

Figure 6:
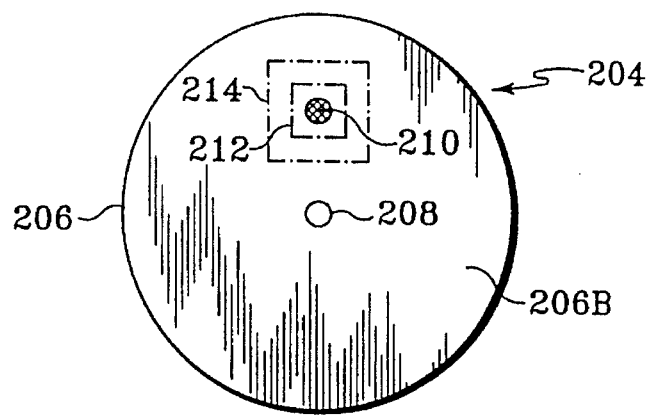
FIGS. 6, 7 and 8 show various views of a further embodiment of a cap liner provided by this invention.
Figure 7:
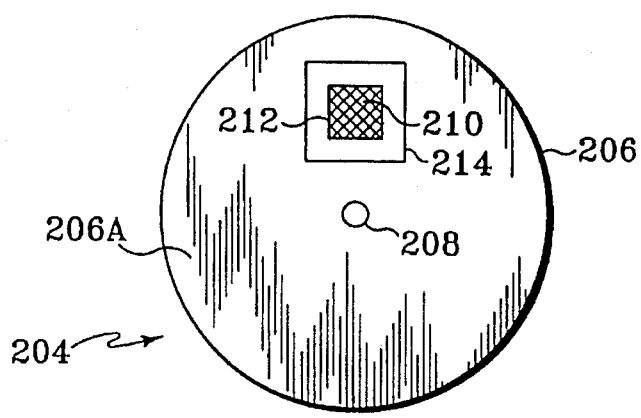
Figure 8:
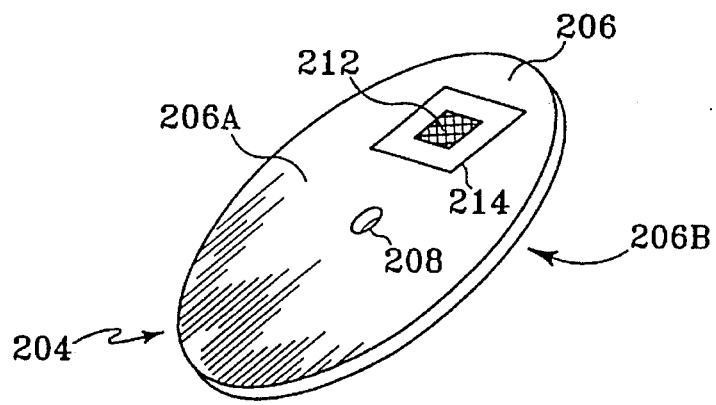

An alternative embodiment of this invention includes a more rigid liner 204 as shown in FIGS. 6–8, which present bottom, top and top-perspective views of liner 204, respectively. Liner 204 is preferably defined by a substantially rigid disk 206 having two or more openings provided therein. The openings of disk 206 are larger than the small openings 104b formed in the gas-permeable membrane of liner 104 shown in FIGS. 4 and 5.

In the embodiment shown in FIGS. 6–8, two openings 208 and 210 are employed wherein one opening, such as central opening 208, allows heated aerosols and fine particulates generated during operation to pass therethrough to the HEPA filter 108 carried by cap 102. As noted above, the HEPA filter permits the passage to atmosphere of air and water vapor from within the processing chamber 20 while blocking aerosols and fine particulates from escaping to atmosphere. While the substantially rigid embodiment shown in FIGS. 6–8 includes two openings 208 and 210, it is understood that more than two openings may be employed so long as the liner 204 is effective in substantially preventing the biological or medical waste being processed from splashing up onto and adhering to the underside of the cap 102. In addition, the openings need not necessarily be located as shown in FIGS. 6–8 with opening 208 located centrally of the disk 206 and opening 210 positioned off-center.

A chemical indicator 212, preferably in patch form, can be disposed over one of the openings such as opening 210 on the top side 206A of the liner 204. Indicator 212 is preferably carried on the top side 206A of liner 204 to be readily observable to personnel when the lid 102 is removed subsequent to the waste treatment cycle while the liner 204 is still positioned atop the upper opening 26 of the apparatus. As noted above, chemical indicator 212 preferably comprises a fibrous, liquid-absorbent material impregnated with chemically sensitive indicator solution that reacts to any decontaminant present in the processing chamber during operation to generate an output, such as a color change or other suitable indicia, indicating that the decontaminant was, in fact, present in the chamber during the treatment cycle. Again, the selection Of an indicator material generally depends upon the decontaminant used to treat the biological and/or medical waste. For example, when used with a decontaminant including peracetic acid, a suitable chemically sensitive indicator is, again, a Peracetic Acid Indicator available from Serim Research, Elkhart, Ind., under the product name "Chronegenic Oxidation Sensitive Indicator."

Indicator 212 preferably has a transparent barrier element 214 disposed over the indicator on the top side 206A of the cap liner 204. Barrier element 214 can be a small piece of transparent adhesive tape generally larger in all dimensions that the indicator patch 212 to prevent any residual liquid from the indicator patch from leaking out. The transparency of barrier 214 allows personnel to readily observe the output signal generated by the indicator without the need to come into contact with the liner. In such an embodiment, the indicator and barrier serve as a "window" into the interior of the processing chamber for the operator to visually confirm that decontaminant was present within the chamber interior during the waste treatment cycle, thus eliminating the need for the operator to access the chamber's interior directly, possibly exposing himself or herself to infectious medical waste and/or residual decontaminant vapor. Decontamination of the chamber contents can thus be confirmed from the output of the indicator by viewing the top of the liner. Once decontamination is confirmed, the contents of the chamber including the liner can be simply poured out for proper disposal without the need for personnel to needlessly expose themselves by handling the cap liner 204.

Barrier 214 also serves to reduce mechanically the rate of liquid saturation of the indicator 212 and to prevent the indicator from becoming fully saturated with water or other liquids prior to its exposure to the decontaminant. Without barrier 214 in place, applicants have discovered that indicator 212 can become fully saturated with liquids other than the decontaminant early in the waste treatment cycle and fail to absorb and thus react to any decontaminant. If the indicator 212 becomes saturated with other liquids, the indicator 212 will typically not accept any further liquid. Applicants believe that it may be possible that barrier 214 provides back pressure through the indicator patch to slow the indicator's saturation rate, thus allowing the decontaminant to be absorbed into the indicator patch even though the indicator may not be exposed to the decontaminant until well into the treatment cycle.

Another advantageous feature of barrier 214 is that it prevents direct contact between the indicator 212 and the underside of lid 102, thus preventing decontaminant residue that may have found its way onto the underside of the lid from a previous cycle from carrying over and tainting a subsequent fresh indicator. In such a scenario, it would be possible that the indicator could generate a false positive output when in fact no decontaminant was present in the interior of the processing chamber during the present waste treatment cycle.

Figure 9:
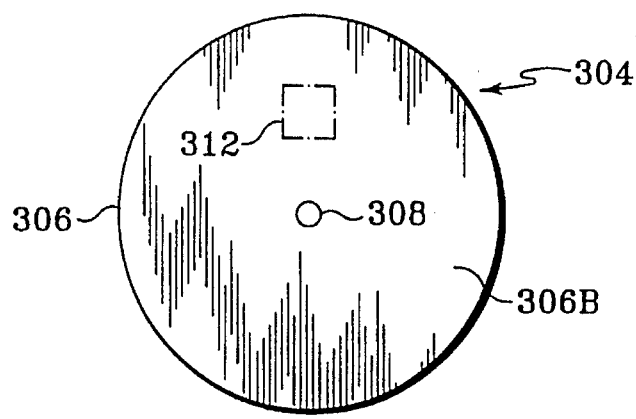
FIGS. 9, 10 and 11 show various views of an even further embodiment of a cap liner provided by this invention.
Figure 10:
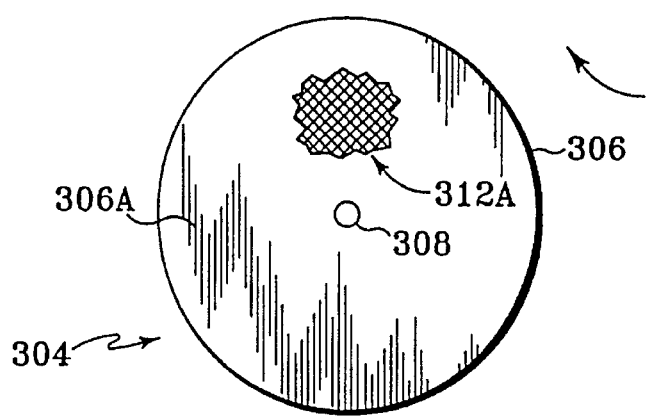
Figure 11:
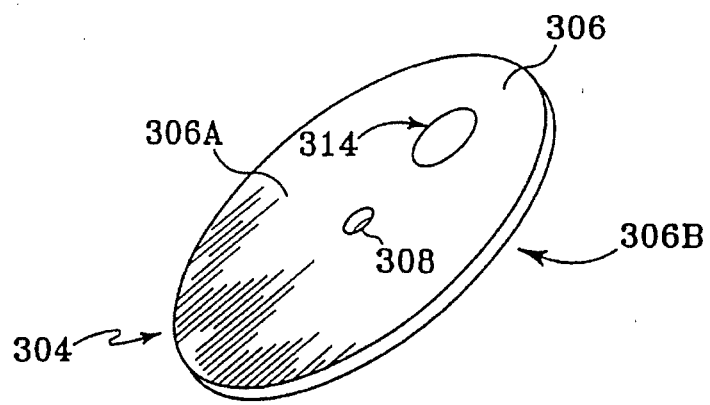

An even further alternative embodiment of this invention is shown in FIGS. 9–11, which present bottom, top and top-perspective views of a semi-rigid liner 304, respectively. Liner 304 is preferably defined by a substantially rigid disk 306 having a liquid-impervious coating applied at least to the bottom side 306B of the liner 304 and having at least one opening 308 provided therein. Opening 308 allows heated aerosols and fine particulates generated during operation of the apparatus to pass therethrough to the HEPA filter 108 carried by the cap 102. While the semi-rigid liner 304 shown in FIGS. 9–11 includes only one opening 308, it should be understood that more than one opening may be employed so long as the liner 304 is effective in substantially preventing the biological or medical waste being processed from splashing up onto and adhering to the underside of the cap 102. In addition, the opening 308 need not necessary be located as shown in FIGS. 9–11 and can be located about other points of the disk so long as the aerosols and fine particulates generated during operation are allowed to pass through to the HEPA filter.

Referring to FIG. 9, cap liner 304 includes an area 312 (shown in phantom lines) on its underside 306B free of the liquid-impervious coating applied to the underside. On the top side 306A of the cap liner 304 in the area generally corresponding to coating-free area 312 on the underside of the disk, a chemically sensitive solution is applied to the liner to soak into and become impregnated into the liner material, which is preferably fiberboard. During the waste treatment cycle, liquids splashing up onto the underside of the liner absorb into the cap liner at the coating-free area 312 on the underside 306B and, as the liquid slowly absorbs into the material, the chemically sensitive indicator solution already impregnated therein chemically reacts with any decontaminant present in the waste liquid and generates an output signal on top side 306A observable from above confirming the presence of decontaminant during the treatment cycle. In this embodiment, the output signal preferably comprises a color signal 312A that appears on the top side 306A of cap liner 304 as shown in FIG. 10. The color signal 312A is readily observable to personnel when the lid 102 is removed subsequent to the treatment cycle while the liner 304 is still positioned atop the upper opening of the treatment apparatus. As previously noted, the selection of a suitable chemically sensitive solution to serve as an indicator material generally depends upon the decontaminant used to treat the biological and/or medical waste. Here again, the coating-free area 312 and output signal 312A serve as a "window" into the interior of the processing chamber for the operator to visually confirm that decontaminant was present within the chamber during the treatment cycle. This eliminates the need for the operator to access the chamber's interior directly and possibly exposing himself or herself to infectious waste and/or residual decontaminant vapor.

The fiberboard material defining the disk 306 has a suitable rate of saturation to prevent the coating-free zone 312 from becoming excessively saturated with other liquids prior to its exposure to decontaminant. This allows decontaminant to be absorbed into the liner material and react with the impregnated chemically sensitive solution, thereby generating an output signal, even though the indicator solution may not be exposed to the decontaminant until well into the treatment cycle.

As shown in FIG. 11, further indicating means 314 defined by a circle or other suitable indicia may be employed where the chemically sensitive solution has been applied to the top side 306A of the liner 304. This provides a reference guide to which personnel can direct their attention to look for an output signal such as 312A shown in FIG. 10. Any reference means may be used on the top side 306A of the liner in this fashion.

Disks 206 and 306 can be constructed of a somewhat rigid plastic or fiberboard material. With respect to fiberboard material, an 18-point fiberboard is suitable. The bottom sides 206A and 306A of the fiberboard disks can be polylaminated with a liquid-impervious plastic or waxy material. If desired, such a liquid-impervious coating can be applied to both the top and bottom sides of the disks. The liners 206 and 306 preferably each have diameters of about 9.156 inches to fit properly atop the upper opening 26 of the waste treatment chamber. Openings 208, 210 and 308 can each have a diameter of about 0.25 inch. In disk 204, opening 210 can be located about 3.0 inches off-center from central opening 208. In liner 304 shown in FIGS. 9–11, opening 308 is preferably located centrally of disk 306. However, as noted above, the relative locations of openings 208, 210 and 308 are not critical for the effective operation of this invention.

The thickness of disks 206 and 306 is generally thin and depends somewhat on the material from which it is made. The disks preferably have sufficient rigidity to be self-supporting when placed over the opening 26 of the processing chamber 20. Where the disk liner is constructed of polylaminated fiberboard, the liner disks preferably have a thickness of about 0.014 inches.

Heat generated within the chamber during operation often creates an expansion of the air and water vapor within the chamber. As indicated above, this apparatus can include a removable filter 108 for permitting the passage of air and water vapor from within the processing chamber 20 while preventing passage of aerosols and fine particulate matter. As shown in FIG. 5, filter 108 includes a lower portion 109 that extends through a central opening (not shown) provided in cap 102. Filter 108 preferably comprises a high-efficiency particulate air (HEPA) filter of the type sold by Gelman Sciences Membrane Filter Division. Portion 109 extends downwardly below the central panel 103 of cap 102 and may be held in place in the opening provided in the cap by an O-ring or other suitable connection means to prevent material from escaping at that interface.

When used in combination with a main power unit such as that described in U.S. Pat. Nos. 5,236,135 and 5,240,187, the portable processing chamber 20 is removed from the main power unit after treatment by simply lifting the processing chamber 20 out of the main power unit by use of the handles 111 or 211, one in each hand. The chamber 20 can then be moved to whatever site location is convenient for disposal of treated waste material therein.

Upon removal of the lid 102 with the liner still atop the upper opening of the processing chamber, personnel can readily observe the chemical indicator to determine if decontaminant was present during the treatment cycle without coming into contact with the cap liner, nor exposing themselves to the possibly infectious interior contents of the chamber. If decontaminant was not present, corrective action can then be taken, e.g., decontaminant can be added and the treatment cycle repeated. If decontaminant was present or decontamination has been effected, the liner will be removed and disposed of automatically without necessitating any human contact or exposure to the interior contents of the chamber by virtue of the liner and treated waste material simply being poured from the processing chamber 20 through its upper opening 26 into suitable containers for proper disposal.

While a presently preferred embodiment and best mode of the invention has been illustrated and described in the drawings and foregoing description, the same is to be considered as illustrative and not restrictive in character. It is to be understood that the invention is defined only by the following claims and the prior art, and that all changes and modifications that come within the scope of the following claims are to be protected thereunder.

What is claimed is:

1. An apparatus for the treatment and decontamination of biological or medical waste, comprising:

a waste treatment chamber having an upper opening formed by an opening interface, said chamber enclosing a rotatable waste treatment assembly accessible through said upper opening;

a lid for engaging said opening interface and closing the upper opening of said chamber to define a closed waste treatment chamber;

a contiguous liner removably carried within the chamber for preventing the waste from adhering to the underside of said lid, said liner having at least one non-deformable opening provided therein sized so as to substantially prevent liquids and solids from passing therethrough while allowing aerosols and entrained particulates to pass therethrough; and a chemical indicator carried by said liner for chemically reacting with any decontaminant present within the chamber and generating an output indicating the presence of the decontaminant within said chamber during the treatment cycle.

2. The apparatus of claim 1 wherein said chemical indicator chemically reacts with any decontaminant present within the chamber during the treatment cycle and changes color during said cycle when the presence of decontaminant is so detected.

3. The apparatus of claim 1 wherein said lid includes a first pressure surface disposed circumferentially about a central panel, wherein said opening interface of the chamber is formed by a second pressure surface of said chamber disposed circumferentially about said opening, and wherein said liner is dimensioned such that, when carried within said chamber, the circumferential edge of said liner is held between the first and second pressure surfaces, thereby releasably securing the liner in position covering the central panel of said lid to prevent waste from adhering to the underside of said lid.

4. The apparatus of claim 1 further comprising a high efficiency particle air filter permitting the passage of air and water vapor from within said chamber, said filter including a portion extending through an opening provided in said lid.

5. The apparatus of claim 1 wherein said liner is constructed of a gas permeable membrane having a plurality of small, non-deformable openings provided therein sized so as to allow aerosols and entrained particulates to pass therethrough while substantially preventing the medical or biological waste being processed by said apparatus from passing therethrough.

6. The apparatus of claim 1 wherein said liner is disposable without human contact thereof upon completion of the decontamination of the waste and the removal of said lid by virtue of its then-unsecured interposition between the lid and upper edge of said chamber and its removal in conjunction with the decontaminated waste while being poured from within said chamber.

7. The apparatus of claim 1 wherein said liner is semi-rigid such that the liner is self-supporting when placed over the upper opening of said waste treatment chamber.

8. The apparatus of claim 1 wherein said liner comprises:

a disk having a top side, a bottom side, and at least one non-deformable opening of fixed size and shape formed therein, the bottom side of said disk being coated with a liquid-impervious coating except for a preselected area of said bottom side being coating free; and wherein said chemical indicator comprises a chemically sensitive indicator impregnated within the disk disposed generally coinciding with the coating-free area on the bottom side of said disk.

9. The apparatus of claim 8 wherein said at least one opening permits aerosols and fine particulates generated during operation of said waste treatment apparatus to pass therethrough.

10. The apparatus of claim 8 wherein said disk is constructed of fiberboard material.

11. The apparatus of claim 1 wherein said chemical indicator comprises a chemically sensitive solution which has been previously applied to the top side of said liner and allowed to soak into and become impregnated in said liner.

12. The apparatus of claim 11 wherein said impregnated chemically sensitive solution reacts with any decontaminant absorbed through the bottom side of said liner and generates a visible output signal observable from above.

13. The apparatus of claim 1 wherein said liner comprises:

a solid disk having a top side, a bottom side, and at least two non-deformable openings of fixed size and shape formed therein; and wherein said chemical indicator is carried on the top side of said disk covering one of said at least two openings formed therein.

14. The apparatus of claim 13 wherein the second of said at least two openings permits aerosols and fine particulates generated during operation of said apparatus to pass therethrough.

15. The apparatus of claim 13 further comprising a barrier disposed over said indicator.

16. The apparatus of claim 13 wherein said disk is constructed of fiberboard material having a liquid-impervious coating on at least the bottom side of said disk.

17. The apparatus of claim 13 wherein said disk is constructed of a plastic material.

18. The apparatus of claim 1 further comprising a sealing member disposed between said lid and said upper opening of said chamber and around said upper opening for providing a fluid-tight seal about said opening interface.

19. The apparatus of claim 18 further comprising a plurality of latches for securing said lid to said opening interface with said sealing member disposed therebetween.

20. The apparatus of claim 18 wherein said lid comprises a central panel and a circumferential lip for receiving therein said sealing member for engagement with said opening interface.

21. The apparatus of claim 20 wherein said sealing member comprises an elastomeric O-ring, and said opening interface of said chamber is formed by a flange disposed circumferentially about said opening, said flange being dimensioned so as to be received within the circumferential lip of said lid to sealingly engage said O-ring therebetween.

22. The apparatus of claim 18 wherein said waste treatment chamber comprises a bottom and a sidewall with said upper opening at its top, wherein said lid is arranged to carry said sealing member and to set atop the opening interface of said chamber, and wherein said apparatus further comprises means for securing said lid to said chamber and for effecting sealing engagement of said lid, sealing member and opening interface.

23. The apparatus of claim 22 wherein said lid includes a first pressure surface disposed circumferentially about a central panel and the opening interface of said chamber is formed by a second pressure surface of said chamber disposed circumferentially about said opening said liner being carried by said lid through the engagement of said liner by first and second pressure surfaces of said lid and sidewall, and wherein said securing means also effects retention of said liner between said lid and chamber.

24. In a waste treatment apparatus for the treatment and decontamination of biological or medical waste, said apparatus including a generally cylindrical body having a bottom, an upwardly standing sidewall, and an open top with a circumferential upper edge, a removable lid having a generally circular circumferential edge for closing the open top of said apparatus body thereby defining, in combination with said bottom and body, a closeable chamber for the treatment and decontamination of waste by a contained rotatable waste treatment assembly, and means for releasably securing the lid over the open top of said body, the improvement comprising:

a removable contiguous liner interposed between said lid and the upper edge of said chamber body for preventing the waste from adhering to the underside of said lid as a result of the treatment of the waste within said chamber, said liner having at least one non-deformable opening provided therein sized so as to substantially prevent liquids and solids from passing therethrough and allowing only gases and entrained particulates to pass therethrough, said liner being self-supporting when disposed over the open top of said chamber and being secured thereover after the introduction of the waste into said chamber upon securing said lid over the open top of said chamber, said liner being disposable without human contact upon completion of the treatment and decontamination of the waste and the removal of said lid by virtue of its then-unsecured interposition between the lid and upper edge of said chamber and its removal in conjunction with the treated waste being poured from within said chamber.

25. The waste treatment apparatus of claim 24 wherein the improvement further comprises the upper edge of said chamber body and a circumferential edge of said lid providing pressure surfaces for receiving and securing therebetween the outer circumferential edge of said liner.

26. The waste treatment apparatus of claim 24 wherein said liner is constructed of a gas-permeable material having a plurality of fixed openings formed therein sized so as to allow aerosols and entrained particulates to pass therethrough while substantially preventing the solid and liquid waste being processed from passing therethrough.

27. The waste treatment apparatus of claim 24 futher comprising a sealing member interposed between said lid and the upper edge of said chamber body for providing a fluid-tight sealing engagement between said lid and the upper edge of said chamber body.

28. The waste treatment apparatus of claim 27 wherein said sealing member comprises an elastomeric O-ring, and the improvement further comprises the circumferential edge of said lid including a downwardly facing peripheral pressure surface adjoining a downwardly facing U-shaped peripheral O-ring flange, and the upper edge of said chamber body including a upwardly facing peripheral pressure surface adjoining a generally planar annular flange to said sidewall of said chamber body, said downwardly facing peripheral pressure surface of the lid abutting, when the lid is positioned over the open top of the chamber body, the upwardly facing peripheral pressure surface of the upper edge of said chamber body and securing therebetween the outer peripheral edge of the liner so that said liner is retained in position to separate the underside of said lid and the interior of said chamber, said O-ring being disposed within the downwardly facing U-shaped peripheral flange of said cap and being engaged by the generally planar annular flange of the upper edge of said chamber body.

29. The waste treatment apparatus of claim 24 wherein said liner comprises:

a solid disk having a top side, a bottom side, and at least two non-deformable openings formed therein; and a chemical indicator carried on the top side of said disk covering one of said at least two openings.

30. The apparatus of claim 29 wherein the second of said at least two openings allows aerosols and fine particulate matter generated during operation of said waste treatment apparatus to pass therethrough.

31. The apparatus of claim 29 further comprising a transparent barrier disposed over said chemical indicator.

32. The apparatus of claim 29 wherein said disk is constructed of fiberboard material having a liquid-impervious coating disposed on at least the bottom side of said disk.

33. The waste treatment apparatus of claim 24 wherein said liner comprises:

a disk having a top side, a bottom side, and at least one opening of fixed size and shape formed therein, the bottom side of said disk being coated with a liquid-impervious coating except for a preselected area of said bottom side being coating free; and a chemical indicator impregnated within the disk disposed generally coinciding with the coating-free area on the bottom side of said disk.

34. The waste treatment apparatus of claim 33 wherein said at least one opening allows aerosols and fine particulate matter generated during operation of said waste treatment apparatus to pass therethrough.

35. The waste treatment apparatus of claim 33 wherein said disk is constructed of fiberboard material.

36. The waste treatment apparatus of claim 33 wherein said chemical indicator comprises a chemically sensitive solution which has been previously applied to the top side of said disk and allowed to soak and become impregnated in said disk.

37. The waste treatment apparatus of claim 33 wherein said chemical indicator reacts with any decontaminant absorbed through the coating-free area on the bottom side of said disk and generates a visible output signal on the top side of said disk observable from above by an operator.

38. The waste treatment apparatus of claim 24 wherein the improvement further comprises an indicator disposed within the interior of said chamber for indicating when decontamination of the waste in said chamber has been effected.

39. The waste treatment apparatus of claim 38 wherein said indicator comprises a chemically interactive indicator carried by said liner for chemically reacting with any decontaminant present in the interior of said chamber and generating a visible output indicating the presence of decontaminant within said chamber during a waste treatment cycle.

40. The waste treatment apparatus of claim 38 wherein said indicator is carried by the top said liner such that the output indicating the presence of decontaminant within said chamber is visible from above said liner upon the removal of the lid and the liner remaining in position atop the open top of said apparatus.

41. The waste treatment apparatus of claim 38 wherein said indicator comprises a chemically sensitive indicator impregnated into said liner to be visible, upon generating an output signal, from either side of said liner.

42. An apparatus for the treatment and decontamination of biological or medical waste, comprising:

a waste treatment chamber having an upper opening formed by an opening interface, said chamber enclosing a rotatable waste treatment assembly accessible through said upper opening;

a lid for engaging said opening interface and closing the upper opening of said chamber to define a closed waste treatment chamber;

a contiguous liner removably carried within the chamber for preventing the waste from adhering to the underside of said lid, said liner being constructed of gas-pervious material having a plurality of fine non-deformable orifices of fixed shape and sized so as to substantially preventing liquids and solids from passing therethrough while allowing aerosols and entrained particulates to pass therethrough; and a chemical indicator carried by said liner for chemically reacting with any decontaminant present within the chamber and generating an output indicating the presence of the decontaminant within said chamber during the treatment cycle.

43. The apparatus of claim 42 further comprising a sealing member disposed between said lid and said upper opening of said chamber and around said upper opening for providing a fluid-tight seal about said opening interface.

* * * * *